(12) United States Patent
Carell (10) Patent No.: US 10,751,425 B2
(45) Date of Patent: Aug. 25, 2020

(54) SACCHARIDE-MODIFIED NUCLEIC ACID MOLECULES

(71) Applicant: baseclick GmbH, Neuried (DE)

(72) Inventor: Thomas Carell, Krailling (DE)

(73) Assignee: baseclick GmbH, Neuried (DE)

(*) Notice: Subject to any disclaimer, the term of this patent is extended or adjusted under 35 U.S.C. 154(b) by 141 days.

(21) Appl. No.: 15/111,071

(22) PCT Filed: Jan. 15, 2015

(86) PCT No.: PCT/EP2015/050685
§ 371 (c)(1),
(2) Date: Jul. 12, 2016

(87) PCT Pub. No.: WO2015/107115
PCT Pub. Date: Jul. 23, 2015

(65) Prior Publication Data
US 2016/0333364 A1    Nov. 17, 2016

(30) Foreign Application Priority Data

Jan. 15, 2014 (EP) .................................... 14151255

(51) Int. Cl.
*A61K 48/00* (2006.01)
*C12N 15/87* (2006.01)

(52) U.S. Cl.
CPC ............ *A61K 48/005* (2013.01); *C12N 15/87* (2013.01); *C12N 2310/11* (2013.01); *C12N 2310/351* (2013.01)

(58) Field of Classification Search
None
See application file for complete search history.

(56) References Cited

U.S. PATENT DOCUMENTS

2012/0136042 A1*  5/2012  Manoharan ............ C07H 21/02
                                                                514/44 A

FOREIGN PATENT DOCUMENTS

| CN | 101238141 A | 8/2006 | |
|----|----|----|----|
| JP | 2007044012 | 2/2007 | |
| WO | WO-2009024977 A2 * | 2/2009 | ............ A61K 47/54 |

OTHER PUBLICATIONS

Diebold et al (Mannose Polyethyleninnine Conjugates for Targeted DNA Delivery into Dendritic Cells. JBC, 274: 19087-19094, 1999).*

(Continued)

*Primary Examiner* — Medina A Ibrahim
*Assistant Examiner* — Wayne Zhong
(74) *Attorney, Agent, or Firm* — Brinks Gilson & Lione (57) ABSTRACT

The present invention refers to the transfection of cells using a conjugate comprising at least one saccharide residue at least one nucleosidic component selected from nucleic acids, nucleosides and nucleotides. This conjugate is suitable for the transfection of prokaryotic and eukaryotic cells such as plant cells or mammalian cells including human cells with high efficacy. Thus, a new delivery vehicle for therapeutic molecules including antisense molecules, sRNA molecules, miRNA molecules, antagomirs or precursors of such molecules, as well as the therapeutic nucleosides or nucleotides, is provided. Further, a convenient strategy for developing new lines of plants that exhibit particular traits is provided.

12 Claims, 7 Drawing Sheets

Specification includes a Sequence Listing.

(56) References Cited

OTHER PUBLICATIONS

Jadhav (Covalent Conjugates of Therapeutic Oligonucleotides for In Vivo Targeting. Doctoral thesis, University of Turku, Finland, p. 1-73, 2017).*
Avino et al (Synthesis and in vitro inhibition properties of siRNA conjugates carrying glucose and galactose with different presentations. Mol Divers. 15:751-757, 2011).*
Yamada et al (Versatile Site-Specific Conjugation of Small Molecules to siRNA Using Click Chemistry. J. Org. Chem. 76, 1198-1211, 2011).*
Yamada et al (Versatile Site-Specific Conjugation of Small Molecules to siRNA Using Click Chemistry. J. Org. Chem. 76, 1198-1211, 2011) (Year: 2011).*
Avino et al (Synthesis and in vitro inhibition properties of siRNA conjugates carrying glucose and galactose with different presentations. Mol Divers. 15:751-757, 2011). (Year: 2011).*
Juliano et al (The Chemistry and Biology of Oligonucleotide Conjugates. Acc Chem Res. 45(7): 1-16, 2012). (Year: 2012).*
Avino et al., "Synthesis and in vitro Inhibition Properties of siRNA Conjugates Carrying Glucose and Galactose with Different Presentations," Molecular Diversity, vol. 15, No. 3, (2011), pp. 751-757.
Pourceau et al., "Synthesis of Mannose and Galactose Oligonucleotide Conjugates by Bi-Click Chemistry," The Journal of Organic Chemistry, vol. 74, No. 3, (2009), pp. 1218-1222.
Yamada et al., "Versatile Site-Specific Conjugation of Small Molecules of siRNA Using Click Chemistry," The Journal of Organic Chemistry, vol. 76, No. 5, (2011), pp. 1198-1211.
International Search Report, issued in PCT/EP2015/050685, dated Mar. 27, 2015.
International Preliminary Report on Patentability, issued in PCT/EP2015/050685, dated Jul. 19, 2016.
Neuhaus et al., "Transport of Primary Metabolites Across the Plant Vacuolar Membrane," FEBS Letters, vol. 581, No. 12, (2007), pp. 2223-2226.
Wormit et al., "Molecular Identification and Physiological Characterization of a Novel Monosaccharide Transporter from *Arabidopsis* Involved in Vacuolar Sugar Transport," The Plant Cell, vol. 18, (2006), pp. 3476-3490.
An et al., "A Transient RNA Interference Assay System Using *Arabidopsis* Protoplasts," Biosci. Biotechnol. Biochem., vol. 67, No. 12, (2003), pp. 2674-2677.
Office Action, issued in corresponding EP Application No. 15700464.9, dated Sep. 20, 2017.
Office Action, issued in corresponding JP Application No. 2016-543113, dated Nov. 20, 2018.

* cited by examiner siRNA-ligands (SEQ ID NO:3) 5'- GGCCUUUCACUACUCCUAC
(SEQ ID NO:4) 3'- dTdTCCGGAAAGUGAUGAGGAUG

X = F, H

Glucose monoazide (Glu):

(1)

Triglucose monoazide (Triglu):

(2)

β-Cyclodextrine monoazide (Dextr.):

(3)

Anandamide monoazide (AEA):

5'-NNNNNNNNNNNNNNNNNNNNNNNNNNNNOH-3'   ssRNA

T4 RNA ligase, ATP

5'-NNNNNNNNNNNNNNNNNNNNNNNNNNNNpCpO—≡ ligand-N₃ | "Click"

5'-NNNNNNNNNNNNNNNNNNNNNNNNNNNNpCpO—[triazole]-Ligand

Fig. 7

SACCHARIDE-MODIFIED NUCLEIC ACID MOLECULES

This application is a National Stage application of International Application No. PCT/EP2015/050685, filed Jan. 15, 2015. This application also claims priority under 35 U.S.C. § 119 to European Patent Application No. 14151255.8, filed Jan. 15, 2014.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Jan. 14, 2014, and is 675 bytes in size. The sequence listing contained in this .txt file is part of the specification and is hereby incorporated by reference herein in its entirety.

The present invention refers to the transfection of cells using a conjugate comprising at least one saccharide residue and at least one nucleosidic component selected from nucleic acids, nucleosides and nucleotides. This conjugate is suitable for the transfection of prokaryotic and eukaryotic cells such as plant cells or mammalian cells including human cells with high efficacy. Thus, a new delivery vehicle for therapeutic molecules including transcripts, mRNAs, antisense molecules, siRNA molecules, miRNA molecules, antagomirs or precursors of such molecules, as well as the therapeutic nucleosides or nucleotides, is provided. Further, a convenient strategy for developing new lines of plants that exhibit particular traits is provided.

RNA interference is a powerful tool that utilizes short RNA double strands to repress the formation of a particular protein in a cell (1-3). In nature, the silencing RNA molecules are produced from larger transcripts that are cut by the Dicer complex (4). For biotechnological application, however, the RNA molecules (siRNA) are chemically prepared and administered. The idea to use siRNA as therapeutic agents (5), was intensively pursued in the last decade but the major obstacle, the poor cellular uptake of RNA duplexes, could not be overcome (6) Currently, RNA delivery systems as divergent as nanoparticles (7,8), liposomes (9,10), or polycation polymers (11) are under intensive investigation. Despite substantial progress in the field, however, the often still high toxicity (12-14) and low cellular specificity represent problems that are not solved.

Most recently, receptor mediated endocytosis has evolved as an alternative delivery strategy (16-25) that allows targeting of the siRNA to special cell types. The method requires linking the siRNA to a ligand that binds to a cell type specific receptor. This initiates an internalization process leading to the uptake of the RNA-ligand conjugate. Currently, the strategy is most successfully implemented with cholesterol modified RNA (24).

PCT/EP2013/064610, the disclosure of which is incorporated herein by reference, describes a conjugate wherein a polyunsaturated fatty acid residue, such as an arachidonic acid residue, is covalently bound to a nucleosidic component. These conjugates are particularly useful for contacting cells where a cannabinoid receptor is present. In particular, neuronal cells and immune cells can be transfected using this conjugate. However, there still remains a need for a convenient strategy to transfect sensitive cells and in particular those cells that are up to now difficult to transfect.

In the present invention it was discovered that sugar transporter proteins present in the cell membrane of both prokaryotic and eukaryotic cells can be efficiently targeted with saccharide modified oligonucleotides. A corresponding receptor-mediated strategy can be successfully used to transfect a wide variety of sensitive cells.

A first aspect of the present invention is the use of a conjugate comprising a saccharide residue and at least one nucleosidic component in the transfection of cells.

The term "conjugate" also encompasses salts, particularly pharmaceutically acceptable salts, e.g. addition salts with inorganic or organic acids or bases as known in the art.

According to a preferred aspect of the invention, the conjugate comprises a saccharide residue and covalently bound thereto at least one nucleosidic component. According to another aspect, a conjugate for use according to the present invention may comprise at least one nucleosidic component and non-covalently bound thereto a saccharide-modified compound. The term "saccharide-modified compound" refers to any compound comprising at least one saccharide residue and being capable of non-covalently binding to a nucleosidic component, e.g. via electrostatic interaction. Examples of saccharide-modified compounds are polycationic materials such as cationic polymers or cationic liposomes comprising at least one saccharide residue, which may form an ionic conjugate with polyanionic nucleic acid molecules. The saccharide residue may be covalently or non-covalently attached to the compound.

The conjugate for use in the present invention comprises at least one saccharide residue, particularly 1-10, more particularly 1-5 saccharide residues. Even more particularly, the conjugate comprises 1 or 2 saccharide residues. Most particularly, the conjugate comprises 1 saccharide residue. If the conjugate comprises more than one saccharide residue, the saccharide residues may be identical or different.

The nucleosidic component attached to the saccharide residue may be selected from nucleic acids, nucleosides and nucleotides.

In a further particular embodiment, the nucleosidic component attached to the saccharide residue is a nucleic acid molecule, more particularly an RNA molecule.

The conjugate comprises at least one nucleosidic component, particularly 1-25, more particularly 2-20 or 2-10, and even more particularly 2-8, i. e. 2, 3, 4, 5, 6, 7 or 8 nucleosidic components. If the conjugate comprises more than one nucleosidic component, the nucleosidic components may be identical or different.

In one embodiment, the conjugate may comprise
  (i) one saccharide residue and one nucleosidic component, e.g. one nucleic acid molecule,
  (ii) multiple saccharide groups and one nucleosidic component, e.g. one nucleic acid molecule,
  (iii) one saccharide residue and multiple nucleosidic components, e.g. multiple nucleic acid molecules, or
  (iv) multiple saccharide residues and multiple nucleosidic components, e.g. multiple nucleic acid molecules.

In a further particular embodiment, the conjugate comprises 1 saccharide residue and 2-20, particularly 2-8, i.e. 2, 3, 4, 5, 6, 7 or 8 nucleosidic components.

In one embodiment, the conjugate may have a linear structure. Thus, nucleosidic components can be connected in a linear chain, wherein a saccharide residue may be present within the chain, at one end of the chain or at both ends of the chain.

In another embodiment, the conjugate has a branched structure, wherein nucleosidic components are bound to a saccharide residue via a branched linker, e.g. a dendrimeric linker.

The term "saccharide residue" includes monosaccharides, disaccharides and oligosaccharides. Examples for monosaccharide residues are glucose, mannose, galactose, ribose, arabinose, fructose, fucose and sialic acid. Disaccharides include for example sucrose, lactose, trehalose and maltose. Oligosaccharides that can be used as saccharide residues in terms of the present invention include linear, branched or circular oligosaccharides. The oligosaccharides typically contain a small number (three to nine) monosaccharide units. A particularly preferred example for circular oligosaccharides is cyclodextrin.

The saccharide residue may be covalently bound to at least one nucleosidic component. Preferably, the saccharide residue is bound to the at least one nucleosidic component via a linker. The linker may be a linear or a branched linker and usually has a chain length of from 2-50 atoms, including carbon atoms and particularly heteroatoms such as S, N, and/or O-atoms.

For example, the linker may be a linear linker, e.g. a linker comprising at least one, e.g. from 1-10, particularly from 2-5 and more particularly 3 $C_1$-$C_3$ alkylene oxide groups, particularly ethylene oxide groups.

Alternatively, the linker may be a branched, e.g. dendrimeric linker.

The saccharide residue may be connected to the at least one nucleosidic component via known linker techniques. Preferably however, the attachment involves a Click reaction, e.g. between an azide and an alkyne group, between a constrained alkene, e.g. a norbornene and a nitrile imine, a nitrile oxide, or a tetrazine, thereby resulting in a cyclic group formed by the Click reaction, particularly a 1,2,3-triazole group.

In a particular embodiment, the conjugate for use according to the present invention is represented by the general Formula (Ia) or (Ib)

$$F_n\text{-}(L_m\text{-}N)_r \quad \text{(Ia)}$$

$$F_n\text{-}(L_m\text{-}N)_r\text{-}L_m\text{-}F_n \quad \text{(Ib)}$$

wherein
F is a saccharide residue,
L is a linker,
N is a nucleosidic component selected from nucleic acids, nucleosides and nucleotides,
n is an integer from 1-10, preferably from 1-5, more preferably 1,
m is 0 or 1,
r is an integer from 1-25,
    preferably from 2-20 and
        more preferably from 2-8.

In this embodiment, the conjugate may be represented by structures such as:

F-L-N

F-(L-N)$_r$ wherein F, L, N and r are as defined above,

F-L*-(N)$_r$ wherein L* is a branched linker and F, N and r are as defined above, F-(L-N)$_r$-L-F wherein F, L, N and r are as defined above.

In another embodiment, the conjugate may comprise a further receptor ligand, covalently bound to the at least one nucleosidic component. The further receptor ligand is a compound different from a saccharide residue such as folate, cholesterol, a hormone or a polyunsaturated fatty acid residue, particularly an arachidonic acid residue such as anandamide.

In this embodiment, the conjugates may be represented by a structure having the general Formula (II)

$$F_n\text{-}(L_m\text{-}N)_r\text{-}L_m\text{-}Z_s \quad \text{(II)}$$

wherein
F is a saccharide residue,
L is a linker,
n is an integer from 1-10, preferably from 1-5, more preferably 1,
m is 0 or 1,
N is a nucleosidic component selected from nucleic acids, nucleosides and nucleotides,
r is an integer from 1-25,
    preferably from 2-20 and
more preferably from 2-8,
Z is a further receptor ligand, and
s is an integer from 1-10, preferably from 1-5, more preferably 1.

In this embodiment, the conjugate may be represented by structures such as:

F-L-N-Z

F-(L-N)$_r$-L-Z wherein F, L, N, Z and r are as defined above,

F-L*-(N)$_r$-L-Z

L* is a branched linker and F, L, N, Z and r are as defined above.

The conjugate for use in the present invention comprises at least one nucleosidic component selected from nucleic acids, nucleosides and nucleotides.

The term "nucleic acid" encompasses single-stranded and double-stranded nucleic acid molecules, e.g. DNA molecules or RNA molecules and analogues thereof. An analogue of a nucleic acid is a nucleic acid molecule which comprises at least one modified building block as described below. In one embodiment, the nucleic acid molecule is a DNA molecule which may comprise at least one modified building block. The term "DNA molecule" encompasses single-stranded or double-stranded DNA molecules. In double-stranded DNA molecules, the individual strands may be present in separate molecules or being covalently connected via a single-stranded loop or via heterologous linker.

The term "DNA molecule" encompasses molecules consisting of natural DNA building blocks, i.e. 2'-deoxyribonucleotide building blocks, and molecules comprising at least one modified building block.

In a further embodiment, the nucleic acid molecule is an RNA molecule, which may comprise at least one modified building block. The term "RNA molecule" encompasses single-stranded or double-stranded RNA molecules, wherein double-stranded RNA molecules may have at least one overhang, e.g. at least one 3'-overhang. In double-stranded RNA molecules, the individual strands may be present as separate molecules or being covalently connected via a single-stranded loop or via a heterologous linker.

The term "RNA molecule" encompasses molecules consisting of natural RNA building blocks, i.e. 2'-ribonucleotide building blocks, and molecules comprising at least one modified building block.

Modified building blocks may be selected from sugar-, backbone- and/or nucleobase-modified building blocks. Sugar-modified deoxyribonucleotides comprise a sugar group different from deoxyribose, e.g. a modified deoxyribose group, wherein the 2'—H group is replaced by a group selected from OH, R, OR, halo, SH, SR, $NH_2$, NHR, $NR_2$ or CN, wherein R is $C_1$-$C_6$ alkyl or alkoxy, or $C_2$-$C_6$ alkenyl or alkynyl and halo is F, Cl, Br, I. Specific examples of 2'-H modifications are 2'-F and 2'-O methyl. Sugar-modified ribonucleotides comprise a sugar group different from ribose, e.g. a modified ribose group, wherein the 2'—OH group is replaced by a group selected from H, R, OR, halo, SH, SR, $NH_2$, NHR, $NR_2$ or CN, wherein R is $C_1$-$C_6$ alkyl or alkoxy, or $C_2$-$C_6$ alkenyl or alkynyl and halo is F, Cl, Br, I. Specific examples of 2'-OH modifications are 2'-F and 2'-O methyl. In a backbone-modified building block, the phosphoester group connecting adjacent building blocks may be replaced by a modified connecting group, e.g. a phosphorothioate group. In nucleobase-modified building blocks, a non-naturally occurring nucleobase may be present instead of a naturally occurring nucleobase. Corresponding analogues of purine or pyrimidine nucleobases are well known in the art. It should be noted that the above modifications may be combined.

The nucleic acid molecule is preferably selected from nucleic acid molecules which are suitable for pharmaceutical applications, particularly from antisense molecules, or from RNA molecules capable of mediating RNA interference such as sRNA molecules or precursors thereof. Further suitable RNA molecules include miRNA molecules, antagomirs, ribozymes and precursors thereof. Also preferred are RNA-transcripts, such as in particular mRNA.

The term "nucleosidic component" also encompasses nucleosides or nucleotides and analogues thereof. A nucleoside is a compound comprising a nucleobase and a sugar group. A nucleotide compound is a compound comprising a nucleobase, a sugar group and a phosphate group. Sugar-, phosphate- and nucleobase-modified compounds are also encompassed by the present invention, particularly nucleoside or nucleotide analogue therapeutics which are suitable for the treatment of cancer and/or viral infections, such as AZT, aciclovir, ganciclovir, valaciclovir, gemcitabine, cytarabine, etc.

The nucleosidic component may be connected to the saccharide residue via a nucleobase, a sugar, or a phosphate group of the molecule. If the compound is a nucleic acid, it may be connected via a building block present in the nucleic acid molecule, particularly via a terminal building block, i.e. a building block located at the 5'- or at the 3'-terminus of a nucleic acid strand. In a preferred embodiment, the connection occurs via a modified terminal nucleobase present in a nucleic acid molecule, particularly in an RNA molecule. According to a particularly preferred embodiment, the saccharide residue is covalently bound to the 5'- or 3'-terminal building block of an RNA transcript, such as in particular mRNA. These conjugates proved to be especially suitable for transfecting plant cells and conferring any desired trait to a plant of interest.

In a preferred embodiment, the covalent linkage to the saccharide residue may be attached to a nucleobase present in the nucleosidic component, e.g. of a building block of a DNA or RNA molecule, e.g. to position 8 of a purine base or to position 5 of a pyrimidine base.

A nucleic acid molecule, e.g. a DNA or RNA molecule, usually has a length of from 5, 10, 12, 15 or 18 building blocks and up to 25, 30, 50 or 100 building blocks or more. The nucleic acid molecule may be prepared by chemical synthesis or by enzymatic methods from nucleic acid templates, e.g. by transcription, catalysed by an RNA polymerase, e.g. by T3, T7 or SP6 RNA polymerase, or by DNA replication or by reverse transcription. Preferably, during chemical or enzymatic synthesis, a building block is incorporated comprising a functional group, e.g. a Click-functional group, e.g. a terminal alkyne group, or an azide group, a constrained alkene group, such as a norbornene group, a nitrile oxide group, a nitrile imine group or a tetrazine group. In a particular embodiment, a building block which is modified by including a terminal alkyne group, optionally via a linker, is incorporated. Methods of introducing Click-modified building blocks into nucleic acid molecules are described in WO2006/117161 and WO2008/052775, the contents of which are herein incorporated by reference. The functional group on the nucleosidic component may be coupled to a complementary functional group which is attached to the polyunsaturated fatty acid residue according to known methods. Preferably, the coupling is carried out by e.g. a Click-reaction with a complementary Click-functional reactive group, e.g. an azide group.

Alternatively, a modified nucleic acid building block linked to the saccharide residue may be introduced into a nucleic acid, e.g. an RNA molecule, during a solid phase synthesis according to standard methods, e.g. using a phosphoramidite building block.

A conjugate for use according to the invention can be prepared from a reagent having the general formula (V)

$F_n$-(L')$_m$-(RG1)$_r$ (V)

wherein

F, n, m and r are as defined above,

L' is a linker, and

RG1 is a reactive group, particularly a Click-reactive group such as an azide group (or an alkyne group).

A further reagent for manufacturing a nucleic acid conjugate for use according to the invention, is represented by the general formula (VI):

BB-(L)$_m$-$F_n$ (VI)

wherein

F, L, n and m are as defined above, and

BB is a building block for synthesizing a nucleic acid molecule, e.g. a nucleoside triphosphate, or a building block suitable for solid phase synthesis, e.g. a phosphoramidite.

Still a further aspect of the present invention is a method of manufacturing a conjugate wherein a saccharide residue is covalently bound to the 3'- or 5'-terminus of an RNA transcript such as mRNA, said method comprising (i) coupling the reagent (V) with at least one modified nucleosidic component (VII)

(N')$_r$-(L")$_m$-RG2 (VII)

wherein

N' is an RNA molecule, e.g. an mRNA molecule,

L" is a linker, r and m are as defined as above

RG2 is a reactive group capable of reacting with RG1, particularly a Click-reactive group such as an alkyne group (or an azide group), thereby forming the conjugate, or (ii) coupling the reagent (V) with at least one modified nucleic acid building block (VIII)

BB-(L")$_m$-RG2 (VIII)

wherein

BB is a building block for synthesizing an RNA molecule,

L" is a linker, m is 0 or 1, and

RG2 is as defined above, thereby forming the reagent (VI), and incorporating the reagent (VI) into an RNA molecule, e.g. by chemical or enzymatic synthesis, thereby forming the conjugate.

A further aspect of the present invention relates to a method of mediating target-specific nucleic acid modifications in a cell or an organism comprising the steps:
(a) contacting a cell or organism with the conjugate of the invention, under conditions, wherein target-specific nucleic acid modifications may occur, and
(b) mediating a target-specific nucleic acid modification effected by the nucleosidic component of the conjugate towards a target nucleic acid.

Contacting step (a) may comprise introducing the conjugate into a target cell, e.g. an isolated target cell, which may be present in a cell culture, a unicellular micro-organism, or a target cell, or a plurality of target cells within a multicellular organism. The target cell is preferably a eukaryotic cell, in particular a mammalian cell, including a human cell or a plant cell. The target organism is preferably a plant or a mammalian organism, e.g. a human organism. The introducing into an organism may comprise parenteral administration, e.g. by injection or infusion, transmucosal administration or transdermal administration. In case of a transfection of plant cells, it was surprisingly found that the described conjugates including a saccharide residue and covalently bound thereto a nucleosidic component are taken up by a plant, if the conjugate is added onto the roots of plants. Hence, introducing a conjugate into a plant may comprise administration of the conjugate to the roots.

Mediating step (b) preferably comprises an inhibition of a target nucleic acid, e.g. by RNA interference when using an siRNA conjugate, or by inhibition of mRNA transcription when using an antisense molecule conjugate, or by inhibition of virus or tumor cell replication using a therapeutic nucleoside/nucleotide conjugate.

The conjugate is preferably introduced into a target cell by receptor-mediated endocytosis, more preferably by sugar transporter protein-mediated endocytosis. Thus, the conjugate may be introduced into the target in the absence of a delivery vehicle and/or a transfection reagent.

In one embodiment, the conjugate is used for the transfection of cells in vitro, particularly for the transfection of plant cells or mammalian cells, including human cells in vitro.

In another preferred embodiment, the conjugate is used for the transfection of plant cells in vitro or in vivo.

Surprisingly it has been found that the conjugate of the invention is particularly suitable for the transfection of plant cells expressing sugar transporter proteins. Conjugates, wherein a saccharide residue is covalently bound to the 5'- or 3'-terminus of a single-stranded or a double-stranded RNA molecule, such as mRNA or antisense RNA, can successfully be introduced into plant cells.

Further, conjugates, wherein a saccharide-modified compound is non-covalently bound to a single-stranded or a double-stranded RNA molecule as described hereinabove, have shown to be particularly suitable for transfecting plant cells. For example, non-covalent conjugates, preferably ionic conjugates, comprising a single-stranded or a double-stranded RNA molecule and a saccharide-modified compound can be used.

In a further embodiment the conjugate of the present invention is for use in medicine, particularly in human medicine, but also in veterinary medicine. Thus, the present invention also provides a pharmaceutical composition comprising a conjugate as described above as the active ingredient together with a suitable carrier. For diagnostic or therapeutic applications, the pharmaceutical composition may be in the form of a solution, e.g. a solution for infusion or injection, a cream, ointment, tablet, suspension or the like. The composition may be administered in any suitable way, e.g. by parenteral administration, e.g. injection or infusion, by transmucosal application, or by transdermal application, or by oral, topical, nasal, rectal application, etc.

The pharmaceutical composition may comprise the conjugate as an active agent in non-encapsulated form, e.g. without a delivery vehicle such as a liposome and/or without a transfection reagent.

The conjugate may be used for the down-regulation of genes in a cell or an organism, e.g. viral genes or cellular disease-associated genes, such as oncogenes, or autoimmune or allergic disease-associated genes. Preferred cellular target genes are e.g. the syk gene, which is an autoimmune or allergic disease-associated gene encoding a spleen tyrosine kinase (SYK), which is involved in IgE-dependent inflammatory signalling cascades. The human SYK ortholog is described in UniProt P 43405, the murine SYK ortholog is described in UniProt P 48025. A further preferred target gene is the APP gene which encodes the amyloid precursor protein (APP). The human APP ortholog is described in UniProt P 05067. APP is cleaved by β- or γ secretases into neurotoxic fragments associated with the development of Alzheimer's disease. Preferred viral target genes are genes encoding the N or P protein of viruses of the mononegavirales order such as Ebola virus, measles virus and rabies virus.

A further aspect of the present invention is a method of transfecting a cell, preferably a plant cell, comprising exposing a cell to a conjugate as described hereinabove. The step of exposing a plant cell to a conjugate as defined herein, preferably comprises adding the conjugate to the roots of a plant. It could be observed that the conjugate is then taken up by the plant and transported by the roots. In particular, conjugates wherein a saccharide residue is covalently bound to the 3'- or 5'-terminus of a single-stranded or a double-stranded RNA molecule, such as mRNA or antisense RNA, can successfully be introduced into plant cells using the method of the invention.

Further, conjugates, wherein a saccharide-modified compound is non-covalently bound to a single-stranded or a double-stranded RNA molecule as described hereinabove, have shown to be particularly suitable for transfecting plant cells. For example, non-covalent, e.g. ionic conjugates of a single-stranded or a double-stranded RNA molecule and a saccharide-modified compound can be used. The present invention therefore provides a convenient strategy for developing new lines of plants that exhibit particular traits.

The present invention shall be outlined in more detail by the following Figures and Examples.

EXAMPLES

1. Synthesis of RNA-Saccharide Conjugates

Figure 1:
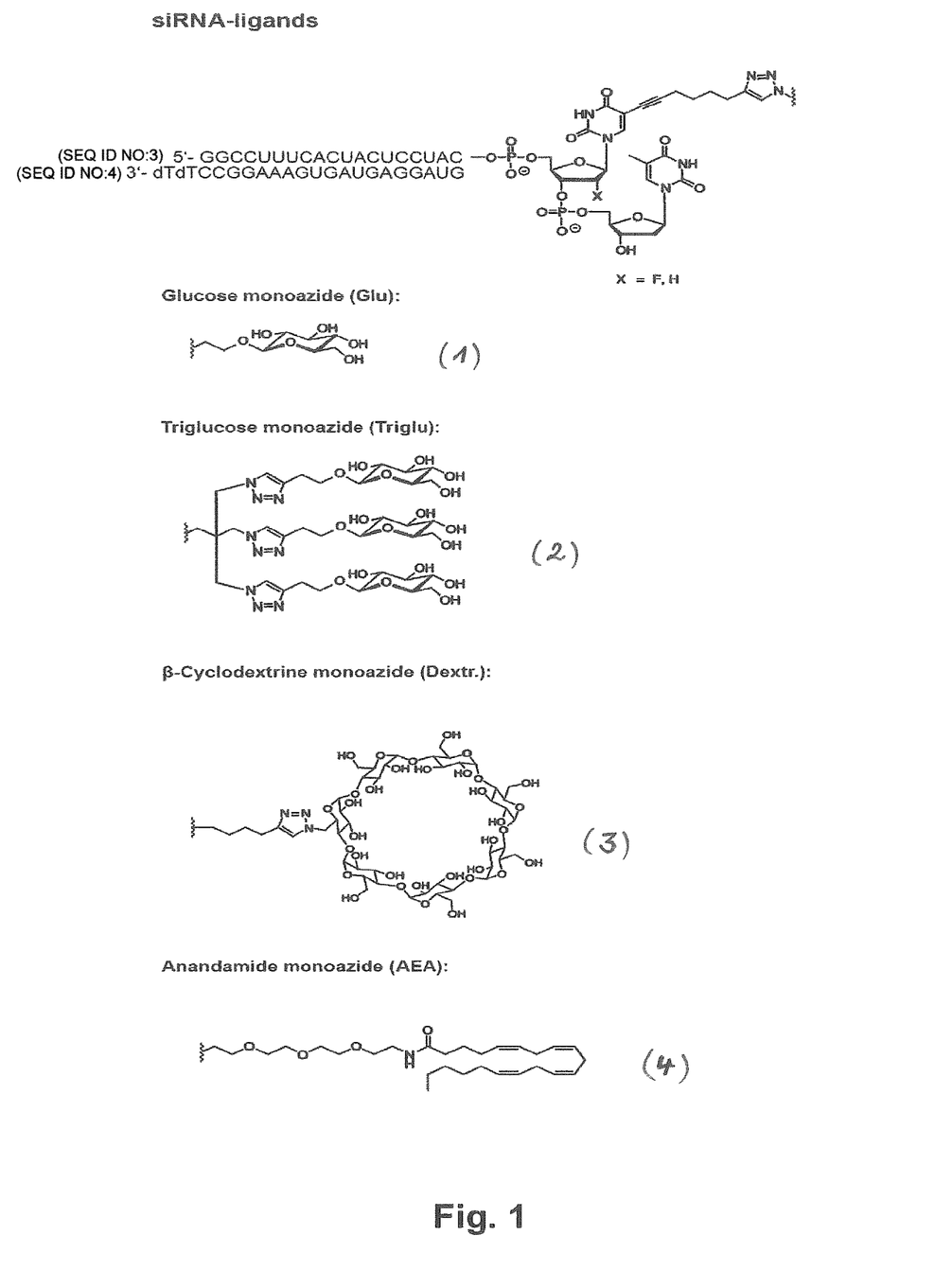
FIG. 1 Chemical structure and sequence of saccharide modified siRNA. As a comparative example, anandamide modified siRNA is shown.
Figure 4:
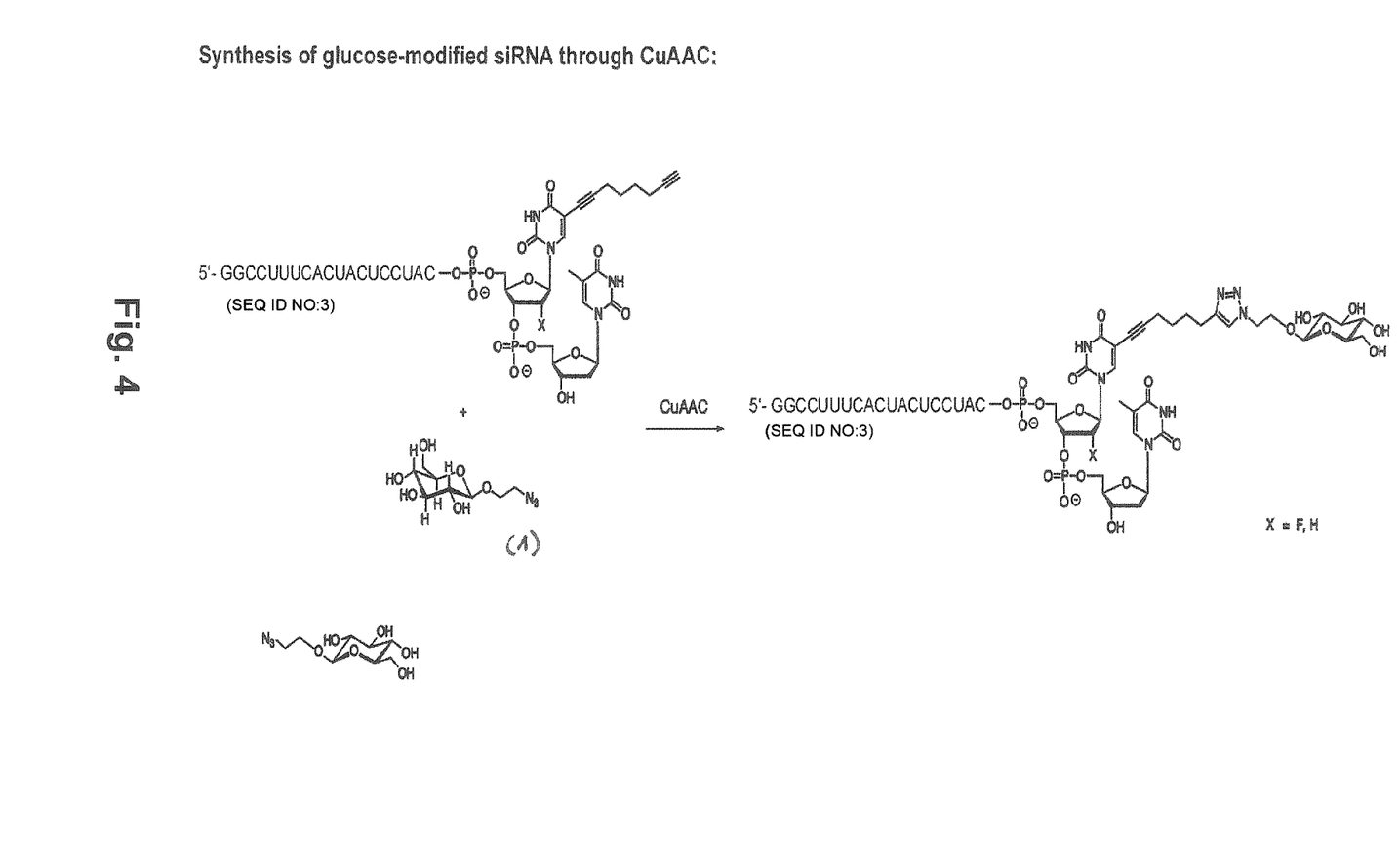
FIG. 4 Synthesis of glucose-modified siRNA through Copper (I)-catalysed Azide-Alkyne Cycloaddition (CuAAC).

The synthesis of the saccharide modified RNA strand was performed as depicted in FIG. 4. The central element of the synthesis is the Cu-catalyzed alkyne-azide click reaction (34-39) between an alkyne modified RNA strand and the corresponding glucose azide 1. In order to compare the glucose modified RNA strands to other systems, the click method was utilized also for the preparation of a triglucose-RNA conjugate using triglucose monoazide 2, and of a β-cyclodextrine modified RNA strand with the β-cyclodextrine monoazide 3. Further, an anandamide modified RNA strand was prepared as a comparative example by using anandamide monoazide (AEA) 4. The respective saccharide residues as well as anandamide monoazide are shown in FIG. 1. In all cases a short ethylene glycol spacer was introduced between the RNA strand and the respective ligand. The click-technology enabled in all cases efficient ligation of the saccharide or ananamide molecules to RNA. In addition, the method enabled efficient conjugation at the more difficult to access 3'-terminus of the siRNA duplex. 3'-modified siRNA strands are typically better tolerated by the RNAi machinery (41). To achieve the 3'-end attachment a deoxyuridine phosphoramidite with an octadiine handle at C5 was used during RNA synthesis.

Figure 3:
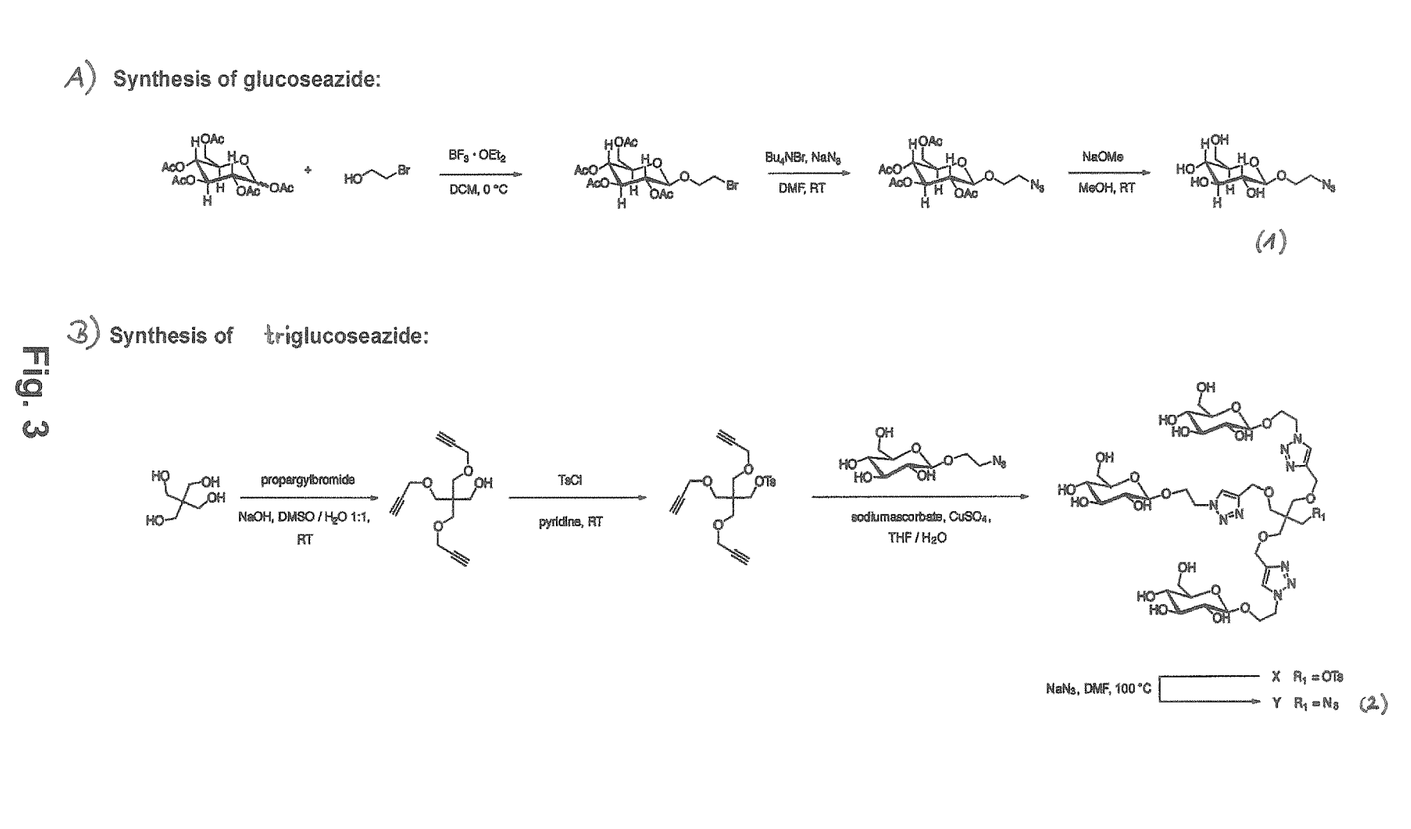
FIG. 3 Synthesis of saccharide-modified reagents. The depicted reaction scheme shows the preparation of glucose azide (A) and triglucoseazide (B).

The synthesis of glucose azide and triglucose azide is shown in FIG. 3. For preparing the glucose azide 1 in a first step, an ethylene glycol spacer was introduced into a protected glucose derivative using 2'-bromoethanol. In a subsequent step, an azide functionality was introduced before the glucose derivative was deprotected to yield glucose azide 1. For the synthesis of the triglucose azide, first a branched linker was prepared from pentaerythrytol and propargyl bromide. Subsequently, after protecting the remaining alcohol functionality, three glucose azides were added in a Click-reaction. Deprotecting the alcohol functionality and introducing another azide functionality finally yielded the triglucose azide 2.

The azides were subsequently clicked with excellent yields to obtain an alkyne-containing RNA sense strand as shown in FIG. 4. After HPLC purification, the saccharide modified RNAs were hybridized to the antisense counter-strand to obtain the siRNA duplexes depicted in FIG. 1.

2. Delivery of RNA-Saccharide Conjugate into Cells

In order to visualize the delivery of the RNA duplexes into living cells the saccharide modified RNA sense strand was initially hybridized to an antisense strand containing a fluorescein label (Alexa=Alexa Fluor® 647, Life Technologies).

Figure 2:
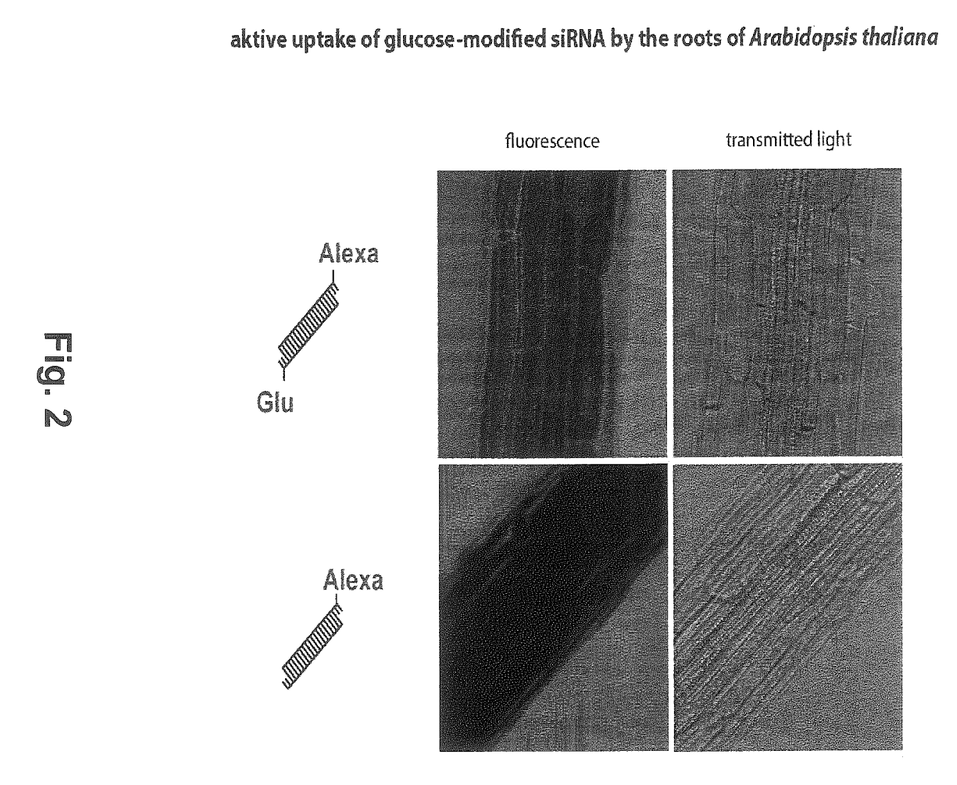
FIG. 2 Delivery of glucose modified siRNA to plant cells. Glucose modified siRNA added onto the roots of *Arabidopsis thaliana* are taken up by the plant and transported along the roots (Alexa=Alexa Fluor® 647, Life Technologies).

Uptake of the glucose modified RNA duplex was studied with *Arabidopsis thaliana* cells. Glucose modified siRNA was added onto roots of *Arabidopsis thaliana*. The confocal microscopy studies depicted in FIG. 2 show that unmodified siRNA is as expected unable to enter the cells. Glucose modified siRNA, however, was readily detected inside the respective cells proving uptake and transport along the roots. The same result was also observed with modified dsDNA (not shown).

Figure 5:
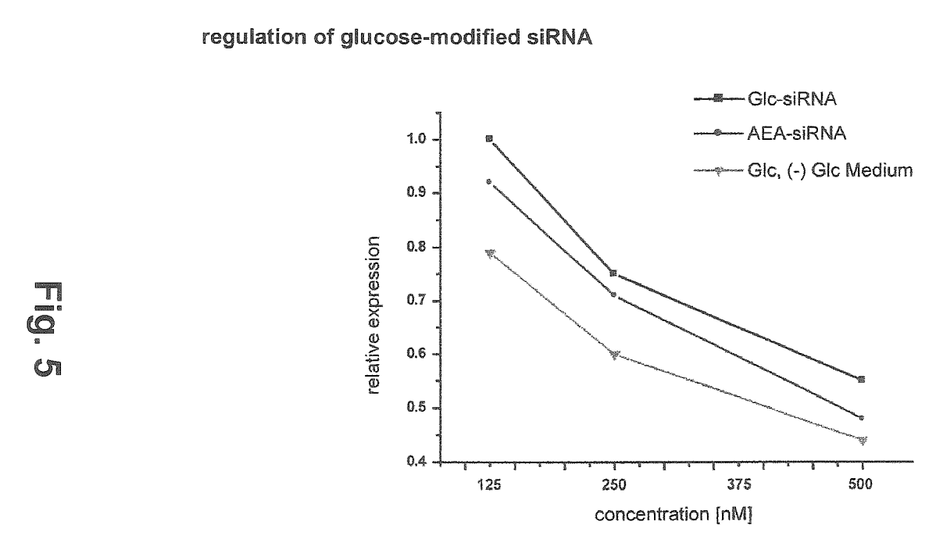
FIG. 5 Relative expression of Renilla-luciferase in RBL-2H3 cells after treatment with glucose-modified siRNA duplex against Renilla-luciferase in comparison to the same siRNA with anandamide-modification (AEA-siRA). The cells were cultured in medium with 11.1 mM glucose (black) or in medium without glucose (green).
Figure 6:
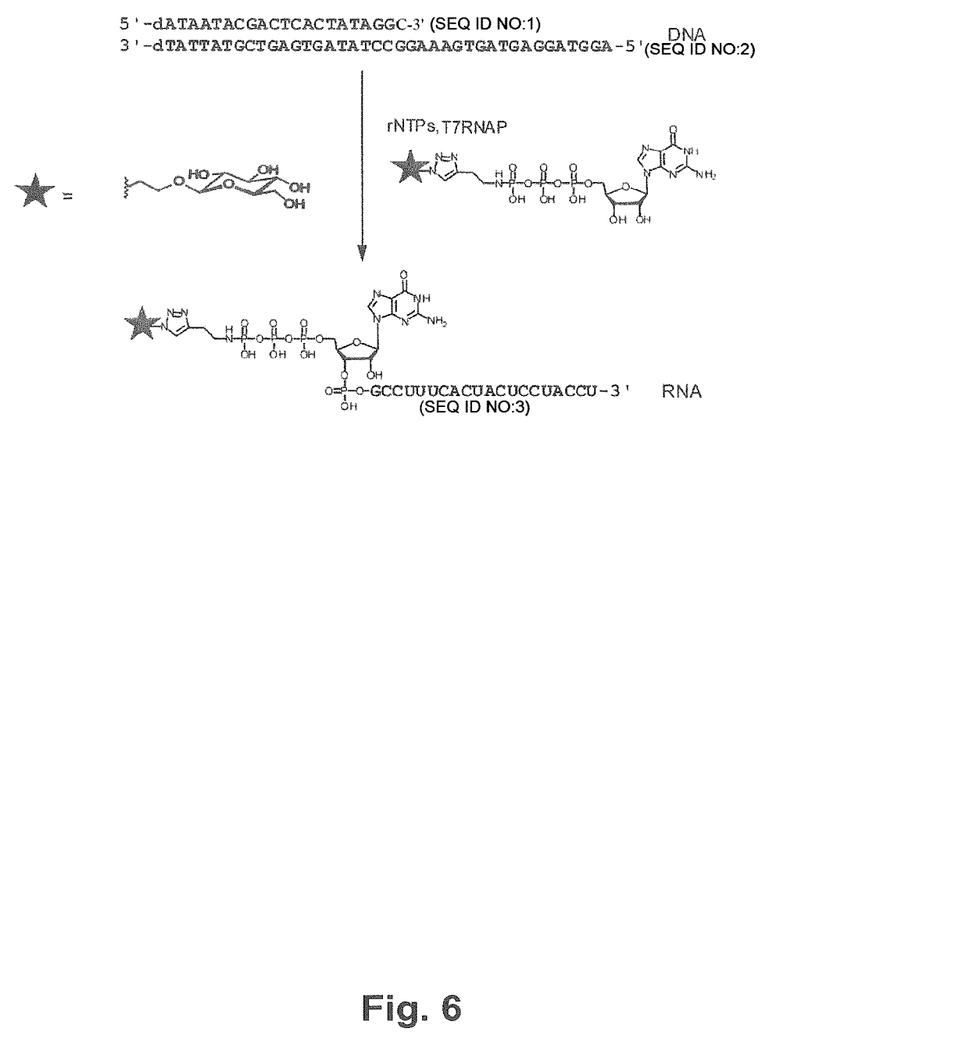
FIG. 6 Principle of the in vitro transcription labelling experiment using T7 RNA polymerase and γ-glucose labelled GTP.

To demonstrate that the delivered siRNA molecules exhibit the desired RNAi effect, a commercially available dual-luciferase reporter assay was utilized. A plasmid containing two luciferases (Renilla and Firefly) was transfected into the cells. RNAi was evaluated by targeting the expression of the Renilla luciferase, whereas the Firefly luciferase served as an internal standard. For these studies the glucose modified siRNA without further fluorescein modification was used. Initial control experiments with unmodified RNA duplexes (no glucose, no fluorescein) showed that the Renilla expression was not affected. In contrast, a dose dependent silencing of Renilla expression in presence of ligand modified siRNA was observed in both cell lines (FIG. 5). Most important, even a relatively low amount of siRNA-ligand conjugate showed already a considerable effect.

The silencing efficacy of glucose modified siRNA was next evaluated in comparison to the ananamide-siRNA conjugate. The result of this comparison is depicted in FIG. 5. Surprisingly, the new glucose modified siRNA is constantly significantly more potent than the ananamide system, which establishes glucose and other saccharide residues as a powerful new delivery tool.

3. 5'-RNA Labelling Using γ-Labelled Nucleotides

For labelling RNA-transcripts at the 5'-terminus, first at 39 mer DNA template bearing the T7 promoter sequence followed by a short encoded transcript was prepared. This allowed a primer independent RNA polymerisation reaction, which results in 21 mer RNA transcript. Due to the de novo initialisation of the polymerase, the first-used RNA nucleotide remains as a triphosphate in the transcript providing a unique 5'-saccharide labelled transcription product. Since the T7 RNA polymerase usually starts on a $CC_n$-sequence, which generates G-starting transcripts, the experiment was performed with glucose-labelled GTP. Despite the presence of the glucose residue, the T7-RNA polymerase accepted the labelled triphosphate and continued the transcription process to give the expected glucose-labelled product.

The following coding and template strand encoding a T7 promotor sequence and a 21mer transcript were purchased from METABION.

```
Coding:
                                        (SEQ ID NO: 1)
5'-dATAATACGACTCACTATAGGC Template:
                                        (SEQ ID NO: 2)
3'-dTATTATGCTGAGTGATATCCGGAAAGTGATGAGGATGGA-5'
```

Prior to the transcriptions, the strands were annealed in a thermocycler (Mastercycler Personal from EPPENDORF). Therefore, 20 μM of the coding strand was annealed to 20 μM of the template strand in buffer (100 mM NaCl, 25 mM Tris-HCl, pH=7.6 at 25° C.) applying the following temperature gradient: 95° C. for 4 min followed by cooling with 2° C./min to 4° C.

In vitro transcriptions were carried out in a 0.2 mL PCR tube in a 20 μL setup. To 40 pmol of the hybridized DNA template in transcription buffer (40 mM HEPES pH=7.4, 6 mM MgCl$_2$, 2 mM, 10 mM DTT), 400 μM ATP, CTP, UTP, 20-80 μM GTP (400 μM for the control) and 400 μM glucose labelled GTP 7d were added. The reactions were started by the addition of one unit T7 RNA polymerase (NEW ENGLAND BIOLABS), carefully mixed and then incubated at 37° C. After 5 h the transcriptions were stopped by addition of one volume RNA loading dye (47.5% formamide, 0.01% SDS, 0.01% bromophenol blue, 0.005% xylene cyanol, 0.5 mM EDTA) and 20 μL of each sample was analyzed on 20% denaturing polyacrylamide gels (7 M urea, 35 mA, 1000 V) and visualized using a LAS-3000 imaging system (RAYTEST). For visualization of RNA transcripts SYBR green II staining was applied.

4. 3'-RNA Labelling Using T4 RNA Ligase

T4 RNA ligase catalyzes the transfer of a cytidine 3', 5'-bisphosphate to the 3'-OH of single-stranded RNA in the presence of ATP.

Figure 7:
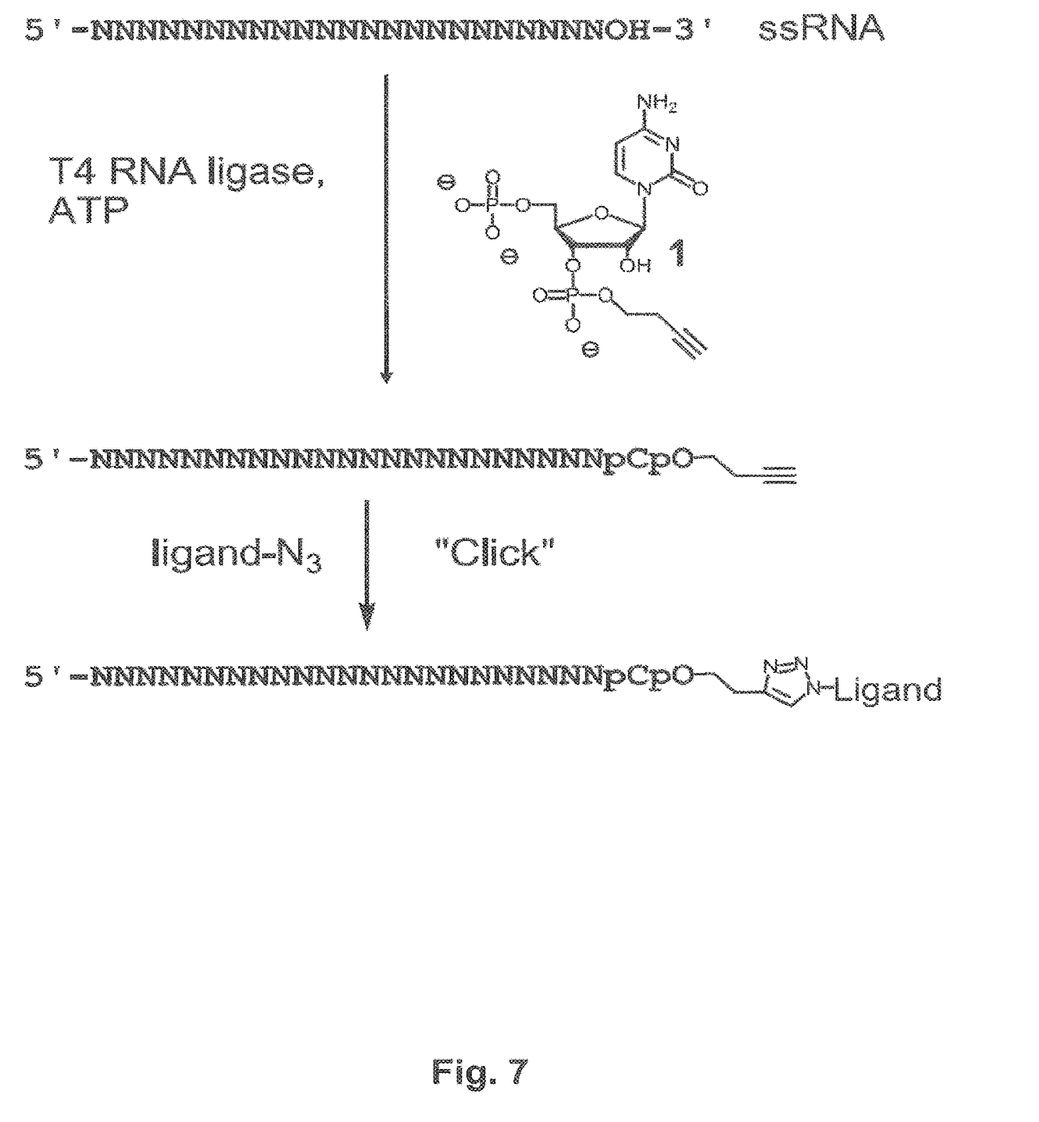
FIG. 7 Regioselective chemo-enzymatic labelling of RNA using T4 RNA ligase.

Thus, a single-stranded RNA molecule may be reacted in the presence of T4 RNA ligase and ATP with a labelled cytidine 3',5'-bisphosphate carrying an alkyne moiety at a phosphate group. A subsequent click-reaction with an azide-modified saccharide residue, as those shown in FIG. 1, allows the preparation of a 3'-modified single-stranded RNA molecule as shown in FIG. 7.

REFERENCES (1) Fire, A. Z. *Angew. Chem. Int. Ed.* 2007, 46, 6966-6984.
(2) Elbashir, S. M.; Harborth, J.; Lendeckel, W.; Yalcin, A.; Weber, K.; Tuschl, T. *Nature* 2001, 411, 494-498.
(3) Mello, C. C. *Angew. Chem. Int. Ed.* 2007, 46, 6985-6994.
(4) Bernstein, E.; Caudy, A. A.; Hammond, S. M.; Hannon, G. J. *Nature* 2001, 409, 363-366.
(5) Castanotto, D.; Rossi, J. J. *Nature* 2009, 457, 426-433.
(6) Tiemann, K.; Rossi, J. J. *EMBO Mol. Med.* 2009, 1, 142-151.
(7) Davis, M. E.; Zuckerman, J. E.; Choi, C. H. J.; Seligson, D.; Tolcher, A.; Alabi, C. A.; Yen, Y.; Heidel, J. D.; Ribas, A. *Nature* 2010, 464, 1067-1070.
(8) Baigude, H.; McCarroll, J.; Yang, C. S.; Swain, P. M.; Rana, T. M. *ACS Chem. Biol.* 2007, 2, 237-241.
(9) Zimmermann, T. S.; Lee, A. C. H.; Akinc, A.; Bramlage, B.; Burncrot, D.; Fedoruk, M. N.; Harborth, J.; Heyes, J. A.; Jeffs, L. B.; John, M.; Judge, A. D.; Lam, K.; McClintock, K.; Nechev, L. V.; Palmer, L. R.; Racie, T.; Röhl, I.; Seiffert, S.; Shanmugam, S.; Sood, V.; Soutschek, J.; Toudjarska, I.; Wheat, A. J.; Yaworski, E.; Zedalis, W.; Koteliansky, V.; Manoharan, M.; Vornlocher, H.-P., MacLachlan, I. *Nature* 2006, 441, 111-114.
(10) Spagnou, S.; Miller, A. D.; Keller, M. *Biochemistry* 2004, 43, 13348-13356.
(11) Urban-Klein, B.; Werth, S.; Abuharbeid, S.; Czubayko, F.; Aigner, A. *Gene Ther.* 2004, 12, 461-466.
(12) Lv, H.; Zhang, S.; Wang, B.; Cui, S.; Yan, J. *J. Control. Release* 2006, 114, 100-109.
(13) Ma, Z.; Li, J.; He, F.; Wilson, A.; Pitt, B.; Li, S. *Biochem. Biophys. Res. Commun.* 2005, 330, 755-759.
(14) Akhtar, S.; Benter, I. *Adv. Drug Deliv. Rev.* 2007, 59, 164-182.
(15) Kurreck, J. *Angew. Chem. Int. Ed.* 2009, 48, 1378.
(16) Nakagawa, O.; Ming, X.; Huang, L.; Juliano, R. L. *J. Am. Chem. Soc.* 2010, 132, 8848-8849.
(17) Alam, M. R.; Dixit, V.; Kang, H.; Li, Z. B.; Chen, X.; Trejo, J.; Fisher, M.; Juliano, R. L. *Nuc. Acids Res.* 2008, 36, 2764-2776.
(18) Alam, M. R.; Ming, X.; Dixit, V.; Fisher, M.; Chen, X.; Juliano, R. L. *Oligonucleotides* 2010, 20, 103-109.
(19) Ming, X.; Alam, M. R.; Fisher, M.; Yan, Y.; Chen, X.; Juliano, R. L. *Nucl. Acids Res.* 2010, 38, 6567-6576.
(20) Oishi, M.; Nagasaki, Y.; Itaka, K.; Nishiyama, N.; Kataoka, K. *J. Am. Chem. Soc.* 2005, 127, 1624-1625.
(21) Leamon, C. P.; Low, P. S. *Proc. Natl. Acad. Sci. U.S.A.* 1991, 88, 5572-5576.
(22) McNamara, J. O.; Andrechek, E. R.; Wang, Y.; Viles, K. D.; Rempel, R. E.; Gilboa, E.; Sullenger, B. A.; Giangrande, P. H. *Nat. Biotech.* 2006, 24, 1005-1015.
(23) Lorenz, C.; Hadwiger, P.; John, M.; Vornlocher, H. P.; Unverzagt, C. *Bioorg. Med. Chem. Lett.* 2004, 14, 4975-4977.
(24) Soutschek, J.; Akinc, A.; Bramlage, B.; Charisse, K.; Constien, R.; Donoghue, M.; Elbashir, S.; Geick, A.; Hadwiger, P.; Harborth, J.; John, M.; Kesavan, V.; Lavine, G.; Pandey, R. K.; Racie, T.; Rajeev, K. G.; Rohl, I.; Toudjarska, I.; Wang, G.; Wuschko, S.; Bumcrot, D.; Koteliansky, V.; Limmer, S.; Manoharan, M.; Vornlocher, H.-P. *Nature* 2004, 432, 173-178.
(25) Nishina, K.; Unno, T.; Uno, Y.; Kubodera, T.; Kanouchi, T.; Mizusawa, H.; Yokota, T. *Mol. Ther.* 2008, 16, 734-740.
(26) Godfray, J.; Estibeiro, P. *Expert Opin. Ther. Targets* 2003, 7, 363-376.
(27) Wood, M. J. A.; Trülzsch, B.; Abdelgany, A.; Beeson, D. *Hum. Mol. Genet.* 2003, 12, R279-R284.
(28) Filion, M. C.; Phillips, N. C. *Biochim. Biophys. Acta, Biomembr.* 1997, 1329, 345-356.
(29) Pertwee, R. G. *Pharmacol. Ther.* 1997, 74, 129-180.
(30) Devane, W. A.; Hanus, L.; Breuer, A.; Pertwee, R. G.; Stevenson, L. A.; Griffin, G.; Gibson, D.; Mandelbaum, A.; Etinger, A.; Mechoulam, R. *Science* 1992, 258, 1946-1949.
(31) McFarland, M. J.; Porter, A. C.; Rakhshan, F. R.; Rawat, D. S.; Gibbs, R. A.; Barker, E. L. *J. Biol. Chem.* 2004, 279, 41991-41997.
(32) McFarland, M. J.; Barker, E. L. *Pharmacol. Ther.* 2004, 104, 117-135.
(33) Glaser, S. T.; Kaczocha, M.; Deutsch, D. G. *Life Sci.* 2005, 77, 1584-1604.
(34) Burley, G. A.; Gierlich, J.; Mofid, M. R.; Nir, S. T. H.; Eichen, Y.; Carell, T. *J. Am. Chem. Soc.* 2006, 128, 1398.
(35) Gierlich, J.; Burley, G. A.; Gramlich, P. M. E.; Hammond, D. M.; Carell, T. *Org. Lett.* 2006, 8, 3639.
(36) Gramlich, P. M. E.; Warncke, S.; Gierlich, J.; Carell, T. *Angew. Chem. Int. Ed.* 2008, 47, 3442.
(37) El-Sagheer, A. H.; Brown, T. *Proc. Natl. Acad. Sci. U.S.A.* 2010, 107, 15329-15334.
(38) Aigner, M.; Hartl, M.; Fauster, K.; Steger, J.; Bister, K.; Micura, R. *ChemBioChem* 2011, 12, 47-51.
(39) Paredes, E.; Das, S. R. *ChemBioChem* 2011, 12, 125-131.
(40) Xia, W.; Low, P. S. *J. Med. Chem.* 2010, 53, 6811-6824.
(41) Wang, Y.; Juranek, S.; Li, H.; Sheng, G.; Wardle, G. S.; Tuschl, T.; Patel, D. J. *Nature* 2009, 461, 754-761.
(42) Ross, T. L.; Honer, M.; Lam, P. Y. H.; Mindt, T. L.; Groehn, V.; Schibli, R.; Schubiger, P. A.; Ametamey, S. M. *Bioconjugate Chem.* 2008, 19, 2462-2470.

(43) Facci, L.; Daltoso, R.; Romanello, S.; Buriani, A.; Skaper, S. D.; Leon, A. *Proc. Natl. Acad. Sci. U.S.A.* 1995, 92, 3376-3380.
(44) Rakhshan, F.; Day, T. A.; Blakely, R. D.; Barker, E. L. *J. Pharmacol. Exp. Ther.* 2000, 292, 960-967.
(45) Wong, B. R.; Grossbard, E. B.; Payan, D. G.; Masuda, E. S. *Expert Opin. Investig. Drugs* 2004, 13, 743-762.
(46) Ulanova, M.; Duta, F.; Puttagunta, L.; Schreiber, A. D.; Befus, A. D. *Expert Opin. Ther. Targets* 2005, 9, 901-921.
(47) Sanderson, M. P.; Gelling, S. J.; Rippmann, J. F.; Schnapp, A. *Cell. Immunol.* 2010, 262, 28-34.
(48) Martin, B. R.; *J. Pharmacol. Exp. Ther.* 2002, 301, 790-796.
(49) S. Munro, K. L. Thomas, M. Abu-Shaar, *Nature* 1993, 365, 61-65
(50) A. B. Lynn, M. Herkenham, *J. Pharmacol. Exp. Ther.*, 1994, 268, 1612-1623.
(51) L. Facci, R. Dal Toso, S. Romanello, A. Buriani, S. D. Skaper, A. Leon, Proc. *Natl. Acad. Sci. U.S.A.* 1995, 92, 3376-3380.
(52) L. A. Matsuda, S. J. Lolait, M. J. Brownstein, A. C. Young, T. I. Bonner, *Nature* 1990, 346, 561-564.
(53) M. Herkenham, A. B. Lynn, B. R. de Costa, E. K. Richfield, *Brain Res.* 1991, 547, 267-274.
(54) B. F. Thomas, X. Wie, B. R. Martin, *J. Pharmacol. Exp. Ther.* 1992, 263, 1383-1390.
(55) T. M. Westlake, A. C. Howlett, T. I. Bonner, L. A. Matsuda, M. Herkenham, *Neuroscience* 1994, 63, 637-652.

---

The invention claimed is:

1. A method of transfecting a cell in vitro, comprising exposing a cell to a conjugate comprising at least one saccharide residue and at least one nucleosidic component,
wherein the nucleosidic component is a nucleic acid molecule comprising 5-100 building blocks and optionally comprising at least one modified building block;
wherein the saccharide residue is covalently bound to a nucleobase of the at least one nucleosidic component via a linker; and
wherein the linker comprises a cyclic group formed by a Click reaction; and wherein the cell is not a human germ cell.

2. The method of claim 1, wherein the saccharide residue is selected from the group consisting of monosaccharides, disaccharides, and linear, branched and circular oligosaccharides.

3. The method of claim 1, wherein the conjugate comprises
(i) one saccharide residue and one nucleosidic component,
(ii) multiple saccharide groups and one nucleosidic component,
(iii) one saccharide residue and multiple nucleosidic components, or
(iv) multiple saccharide residues and multiple nucleosidic components.

4. The method of claim 1, wherein the conjugate comprises a saccharide residue, covalently bound to the 3'- or 5'-terminus of an RNA-transcript.

5. The method of claim 1 for the transfection of plant cells.

6. A method for the down-regulation of genes comprising transfecting a cell in vitro with a conjugate comprising at least one saccharide residue and at least one nucleosidic component,
wherein the nucleosidic component is an inhibitory RNA molecule comprising 5-100 building blocks and optionally comprising at least one modified building block;
wherein the saccharide residue is covalently bound to a nucleobase of the at least one nucleosidic component via a linker; and
wherein the linker comprises a cyclic group formed by a Click reaction; and,
wherein the cell is not a human germ cell.

7. The method of claim 6, wherein the saccharide residue is selected from the group consisting of monosaccharides, disaccharides, and linear, branched and circular oligosaccharides.

8. The method of claim 6, wherein the conjugate comprises
(i) one saccharide residue and one nucleosidic component,
(ii) multiple saccharide groups and one nucleosidic component,
(iii) one saccharide residue and multiple nucleosidic components, or
(iv) multiple saccharide residues and multiple nucleosidic components.

9. The method of claim 1, wherein the nucleosidic component is a nucleic acid molecule comprising 10-50 building blocks and optionally comprising at least one modified building block.

10. The method of claim 1, wherein the nucleosidic component is a nucleic acid molecule comprising 15-25 building blocks—and optionally comprising at least one modified building block.

11. The method of claim 6, wherein the nucleosidic component is an inhibitory RNA molecule comprising 10-50 building blocks and optionally comprising at least one modified building block.

12. The method of claim 6, wherein the nucleosidic component is an inhibitory RNA molecule comprising 15-25 building blocks and optionally comprising at least one modified building block.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Coding strand encoding T7 promoter

<400> SEQUENCE: 1
ataatacgac tcactatagg c                                                 21

<210> SEQ ID NO 2
<211> LENGTH: 39
<212> TYPE: DNA
<213> ORGANISM: Artificial Sequence
<220> FEATURE:
<223> OTHER INFORMATION: Template strand encoding a T7 promoter

<400> SEQUENCE: 2
aggtaggagt agtgaaaggc ctatagtgag tcgtattat                              39

<210> SEQ ID NO 3
<211> LENGTH: 19
<212> TYPE: RNA
<213> ORGANISM: Artificial Sequence
<220> FEATURE:
<223> OTHER INFORMATION: coding strand of saccharide modified siRNA

<400> SEQUENCE: 3
ggccuuucac uacuccuac                                                    19

<210> SEQ ID NO 4
<211> LENGTH: 19
<212> TYPE: RNA
<213> ORGANISM: Artificial Sequence
<220> FEATURE:
<223> OTHER INFORMATION: Template strand of the saccharide modified
      siRNA
<220> FEATURE:
<221> NAME/KEY: misc_feature
<222> LOCATION: (19)..(19)
<223> OTHER INFORMATION: dTdT overhang

<400> SEQUENCE: 4
guaggaguag ugaaaggcc                                                    19
```